US006329142B2

United States Patent
Tsuruoka et al.

(10) Patent No.: US 6,329,142 B2
(45) Date of Patent: *Dec. 11, 2001

(54) ASSAY OF NUCLEIC ACID BY FLUORESCENCE POLARIZATION TECHNIQUE AND DETECTION OF VEROTOXIN-PRODUCING MICROORGANISMS

(75) Inventors: Makoto Tsuruoka, 7024, Otsuka, Numata-machi, Asaminami-ku, Hiroshima-shi; Isao Karube, 1-3-16, Higashiarima, Miyamae-ku, Kawasaki, Kanagawa-shi, both of (JP)

(73) Assignees: Nishikawa Rubber Co., Ltd.; Makoto Tsuruoka, both of Hiroshima; Isao Karube, Kanagawa, all of (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/127,864

(22) Filed: Aug. 3, 1998

(30) Foreign Application Priority Data

Aug. 1, 1997 (JP) .................................................. 9-219744

(51) Int. Cl.[7] .............................. C12Q 1/68; C12P 19/34; C07H 21/04; C07H 21/00
(52) U.S. Cl. ............................ 435/6; 435/91.2; 536/22.1; 536/24.3; 536/25.32
(58) Field of Search ..................... 435/91.2, 6; 536/22.1, 536/24.3, 25.32

(56) References Cited

U.S. PATENT DOCUMENTS 5,210,015 * 5/1993 Gelfand et al. ........................... 435/6
5,445,935 * 8/1995 Royer ...................................... 435/6

OTHER PUBLICATIONS

Tsuruoka et al. Rapid detection of the Escherichia cori verotoxin gene using fluorescence polarization, Nippon Rinsho. Japanese J. of Clinical Medicine, vol. 55(3), pp. 741–746, (translation), 1997.*

McCabe Production of single–stranded DNA by asymmetric PCR, PCR Protocols pp. 76–83, 1990.*

Paton et al. Polymerase chain reaction amplification, cloning and sequencing of variant *Escherichia coli* Shiga–like toxin type II operons, Microbial Pathogenesis, vol. 15, pp. 77–82, 1993.*

Tsuruoka et al. Rapid detection of the *Escherichia coli* verotoxin gene using fluorescence polarization, Japenese J. of clinical medicine, vol. 55(3), pp. 741–746 (Abstract), Mar. 1997.*

Tsuruoka et al, *Nucleic Acids Symposium Series*, 39:115–116 (Sep. 18–20, 1998).

* cited by examiner

Primary Examiner—Kenneth R. Horlick
Assistant Examiner—Joyce Tung
(74) Attorney, Agent, or Firm—Sughrue, Mion, Zinn, Macpeak & Seas, PLLC

(57) ABSTRACT

A method for assaying a nucleic acid comprising amplifying a nucleic acid in a sample by gene amplification and measuring the increased amount of the nucleic acid by a fluorescence polarization technique, in which the gene amplification is carried out by asymmetric amplification, or annealing with the primers used in the amplification is carried out after amplification of the nucleic acid, thereby to facilitate binding of a fluorescence-labeled reagent to the target single-stranded nucleic acid.

6 Claims, 4 Drawing Sheets

LANE 1. POSITIVE (SYM)
2. POSITIVE (ASYM)
3. NEGATIVE (SYM)
4. NEGATIVE (ASYM)
M. 100 BASE-PAIR LADDER DNA MARKER

ASSAY OF NUCLEIC ACID BY FLUORESCENCE POLARIZATION TECHNIQUE AND DETECTION OF VEROTOXIN-PRODUCING MICROORGANISMS

FIELD OF THE INVENTION

This invention relates to a method for rapidly assaying a nucleic acid in a sample amplified by gene amplification by a fluorescence polarization technique. More particularly, it relates to a method for rapidly detecting a Verotoxin-producing microorganism by making use of this assay.

BACKGROUND OF THE INVENTION

The necessity of assaying nucleic acids, the entity of genes, has been increasing. Methods utilizing radioisotopic labels or enzymatic labels have been studied on the model of conventional immunoassay, and some of them have been put into practical use. Most of these conventional methods for nucleic acid assay are based on a heterogeneous system. That is, a sample containing a nucleic acid to be assayed is mixed with a reagent to cause a reaction, separating the reacted substance or reagent (bound form) and unreacted substance or reagent (free form) (called B/F separation), and measuring signals sent from the label. The B/F separation is carried out by the use of a DNA reagent or magnetic fine particles or by electrophoresis. Any of these known B/F separation techniques require complicated or time-consuming operations.

A fluorescence polarization technique is known to be applicable to homogeneous assay systems which do not involve the B/F separation. While this technique has been known as a simple, easy and rapid method for determining a drug, etc. in a sample, it is deemed applicable to the assay of nucleic acids as well (see Unexamined Published Japanese Patent Application No. 5-123196).

In carrying out the assay of nucleic acid by the fluorescence polarization technique, a nucleic acid containing a base sequence complementary to the nucleic acid to be detected is labeled with a fluorescent substance to prepare a fluorescence-labeled reagent (also called a labeled probe). A single-stranded nucleic acid is usually used as a reagent.

An example of nucleic acid assay by a fluorescence polarization technique is as follows. A fluorescence-labeled reagent is added to a sample for assay. If the sample contains a nucleic acid having a target base sequence, the site of the nucleic acid having that base sequence is engaged and bound to the complementary reagent. This reaction is called hybridization. The nucleic acid in the sample should previously be denatured by heat treatment or treatment with a chemical so as to have a single-stranded structure. Upon hybridization between the fluorescence-labeled reagent and the target nucleic acid, the apparent molecular weight of the reagent increases. In general, movement of molecules in a solution becomes slower as the molecular weight increases. Therefore, the degree of fluorescence polarization after hybridization is higher than before hybridization because of the increase of the fluorescence-labeled reagent in apparent molecular weight. With the amount of the fluorescence-labeled reagent being fixed, the change in degree of fluorescence polarization is proportional to the amount of the nucleic acid in the sample. Therefore, the amount of the target nucleic acid in the sample can be measured from the change in degree of fluorescence polarization by the reaction.

The degree of fluorescence polarization is usually measured by setting a polarizer on both the exciting side and the fluorescence side, rotating the polarizer on the fluorescence side, and measuring fluorescence whose plane of polarization is parallel to the plane of polarization of the exciting light and fluorescence whose plane of polarization is perpendicular to the plane of polarization of the exciting light. Therefore, one measurement is completed within such a short time as 1 minute.

As stated above, a fluorescence polarization technique does not require B/F separation and is expected to establish a rapid and easy method for assaying nucleic acids. However, the detection sensitivity of this method is not so high as expected because the technique essentially relies for its sensitivity on the detection sensitivity of the fluorescence-labeled substance. Further, in many cases in which a sample taken from a patient or a food is examined, the amount of the nucleic acid, if any, is so small that the sensitivity of the fluorescence polarization technique is not enough.

It may be easily assumed that the sensitivity could be improved by amplifying the genes (nucleic acids) of the target microorganism by gene amplification such as the PCR method as taught, e.g., in Erlich, H. A., Gelfand, D. H. and Saiki, R. K., *Nature*, Vol. 331, pp. 461–462, "Specific DNA Amplification" (1988). It has also been proposed to use a fluorescence-labeled oligoDNA as a primer for amplification of a gene nucleic acid so as to increase the degree of fluorescence polarization with the progress of amplification as reported in Tamiya, E. and Karube, I., *New Functionality Materials* B, pp. 99–104 (1993).

As mentioned above, it is expected that the amount of a nucleic acid, such as deoxyribonucleic acid (DNA), is increased by gene amplification and the amplification product can be detected by the fluorescence polarization technique.

However, in experimentation on DNA in which DNA is amplified by a usual polymerase chain reaction (PCR) technique (see Erlich, H. A., Gelfand, D. H. and Saiki, R. K., *Nature*, Vol. 331, pp. 461–462, "Specific DNA Amplification" (1988)), and the amplified DNA is assayed as such by the fluorescence polarization technique, the results obtained have often turned out still insufficient in detection sensitivity or poor in reproducibility.

SUMMARY OF THE INVENTION

An object of the present invention is to overcome the disadvantage of the conventional techniques and to provide a method for assaying a nucleic acid in a sample having been amplified by gene amplification accurately, rapidly, and with good reproducibility by making use of fluorescence polarization.

Another object of the present invention is to provide a method for rapidly detecting a Verotoxin-producing microorganism, such as *E. coli* O-157, by using the above method.

The inventors of the present invention considered that such a disadvantage of the fluorescence polarization technique applied to a nucleic acid amplification product as obtained by usual PCR is ascribable to the following. An amplification product of a nucleic acid as obtained by usual PCR is substantially a complete double-stranded nucleic acid, whereas a fluorescence-labeled reagent used in fluorescence polarization is, in principle, has a relatively short single-stranded structure. When the longer double strand nucleic acid in a sample is denatured into a single-stranded nucleic acid by, for example, heat treatment, and hybridization is tried between the fluorescence-labeled reagent and a target single-stranded nucleic acid that has a base sequence complementary to the labeled reagent, the other single-stranded nucleic acid complementary to the target s—s nucleic acid competes with the fluorescence-labeled reagent, making the hybridization difficult in terms of energy. Thus, a mere combination of a fluorescence polarization technique and a known technique of gene amplification, such as a standard PCR, fails to establish a nucleic acid assay system having good reproducibility and high sensitivity.

As a result of extensive investigations, the inventors have found that the above objects are accomplished by carrying out gene amplification by asymmetric gene amplification thereby to selectively amplify the target single-stranded nucleic acid that has a base sequence complementary to a fluorescence-labeled reagent. According to this method, since the target single-stranded nucleic acid predominates over the other single-stranded nucleic acid, the efficiency in hybridization between the fluorescence-labeled reagent and the target single-stranded nucleic acid is obviously improved.

They have also found that the above objects are accomplished by amplifying the nucleic acid by gene amplification, denaturing the amplified nucleic acid by heat treatment, etc. into a single-stranded nucleic acid, and annealing them with the primers used in gene amplification. According to this method, the denatured single-stranded nucleic acid molecules are prevented from hybridizing among themselves thereby to improve the efficiency of hybridization between the fluorescence-labeled reagent and the target single-stranded nucleic acid.

The present invention makes it possible to measure a nucleic acid present in microorganisms, bacteria and other samples specifically and rapidly and to provide information useful for examination of microorganisms, clinical diagnosis, and other examinations and researches. In particular, the present invention can be used for rapid and accurate detection of enteropathogenic *Escherichia coli* which produces Verotoxin, i.e., VT2-producing *E. coli*, especially *E. coli* O157, and has recently posed a social problem.

Thus, the present invention provides:

(1) A method for assaying a nucleic acid in a sample which comprises amplifying a nucleic acid in a sample by asymmetric amplification, and measuring the amount of the nucleic acid by a fluorescence polarization technique using a fluorescence-labeled reagent which is complementary to the nucleic acid.

(2) The above-described method for assaying a nucleic acid, wherein a single-stranded nucleic acid having a base sequence which is complementary to the fluorescence-labeled reagent is selectively amplified by the asymmetric amplification.

(3) A method for assaying a nucleic acid which comprises amplifying a nucleic acid in a sample by gene amplification, annealing the nucleic acid with the primers used for the amplification, and measuring the amount of the nucleic acid by a fluorescence polarization technique using a fluorescence-labeled reagent which is complementary to the nucleic acid.

(4) The above-described method for assaying a nucleic acid, wherein a reaction solution containing the amplified nucleic acid and the fluorescence-labeled reagent contains 0.01 to 5 mol/l of an organic or inorganic acid salt.

(5) A method for detecting a Verotoxin-producing microorganism in a sample, which comprises detecting a nucleic acid which is specific to a Verotoxin-producing microorganism by the method according to any one of the above-described methods.

(6) The method for detecting a Verotoxin-producing microorganism in a sample according to (5) above, wherein the fluorescence-labeled reagent contains a DNA represented by the base sequence AGTATCGGGGAGAGGATGGTGTC(SEQ ID NO:1).

DETAILED DESCRIPTION OF THE INVENTION

Figure 1:
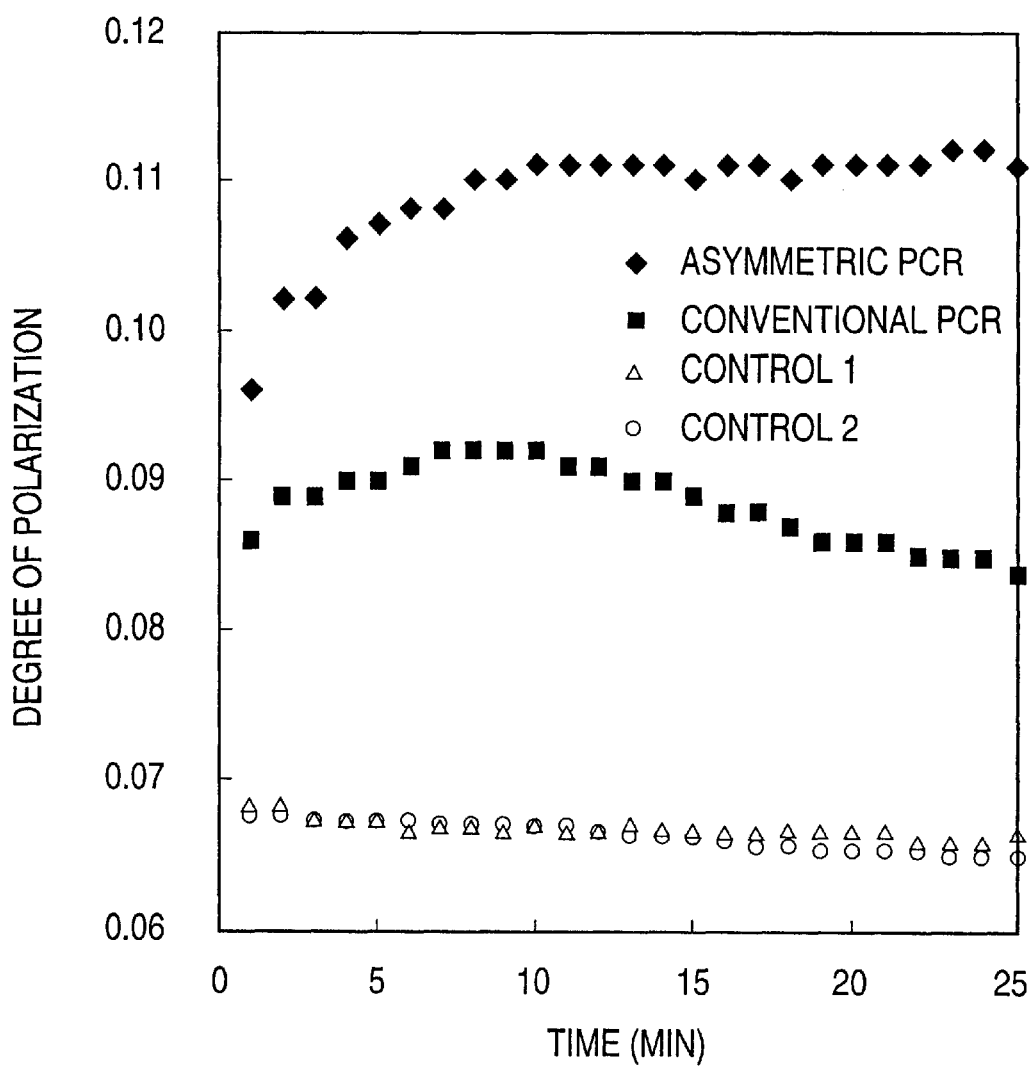
FIG. 1 is a graph showing changes in degree of fluorescence polarization with time in samples assayed in Example 1.

The terminology "nucleic acid" as used herein includes deoxyribonucleic acid (DNA) and ribonucleic acid (RNA).

The terminology "asymmetric amplification (method)" is intended to mean an amplification method in which only one of the two single strands constituting a double strand nucleic acid is selectively amplified or amplification of one of the two single strands is amplified predominantly over the other.

According to conventional PCR, two kinds of primers are added in equal amounts to a sample to induce chain reaction for DNA replication (hereinafter, also referred to as symmetric amplification). Since the DNA to be replicated is usually double-stranded, the replicated DNA is almost double-stranded, too. The asymmetric amplification in the present invention can be carried out in the same manner as the conventional symmetric PCR except that only one of the primers is added or one of the primers is added in a larger amount than the other primer (cf. *Proc. Natl. Acad. Sci., U.S.A.*, Vol. 85, pp. 7652–7656 (1988)). One cycle of the amplification comprises a heat denaturing step, a primer annealing step, and a DNA elongation step. One of the primers which corresponds to the target strand for predominant amplification should be used in a larger amount than the other primer (generally from 2 to 100 times, preferably from 2 to 10 times, as much as the other primer).

Similar to the conventional PCR, it is preferable to control the number of cycles depending on the amount of nucleic acid to be detected. In other words, the number of cycles is increased when the amount of the nucleic acid is low. The number of cycles is not particularly limited and one cycle can be sufficient for amplification in some cases. Generally, 2 to 40 cycles are preferable, and 10 to 40 cycles are more preferable in view of the amplification efficiency.

Nucleic acid can be denatured by, for example, heat treatment at the temperature of from about 95° C. to about 100° C. for several tens of seconds to several minutes or treatment with an appropriate amount of an agent which labilizes hydrogen bonding (e.g., an alkali and formamide). For the gene amplification, denature with heat treatment is preferable. In order to anneal the nucleic acid amplified by the gene amplification method with the primers, it is necessary to first denature the amplified double-strand nucleic acid into a single-stranded nucleic acid by the conventional method as described above.

The conditions for annealing the primers vary depending on their length (number of bases) or base sequence and generally employed conditions can be employed in the present invention (e.g., about 45° C. for about 30 seconds). Generally, higher annealing temperature improves the specificity of the primer binding but deceases the amount of bound primers. On the other hand, lower annealing temperature increases the amount of bound primers to improve the effects of the annealing treatment but deceases the specificity of the primer binding. The conditions for annealing before detection may be the same with the conditions for annealing employed in the gene amplification. When a sample has a sufficient amount of nucleic acid to be detected, the nucleic acid can be assayed by the fluorescence polarization technique after carrying out only the annealing with the primers and without amplification of nucleic acid.

The DNA elongation step in the gene amplification can be carried out in accordance with the conventional method. The conditions for the DNA elongation are appropriately selected taking into consideration the optimum temperature for the DNA polymerase used (preferably, Taq DNA polymerase), pH of the solution, salt concentration, nature of template DNA, etc., but generally the DNA elongation step is carried out by keeping the temperature from about 70° C. to about 75° C. for about 1 minute to about 2 minutes.

In the conventional PCR, the final cycle is stopped by the DNA elongation step at the temperature of about 72° C. for about 5 minutes. However, according to the embodiment of the present invention which employs the annealing treatment, it is not required to stop the cycle at the DNA elongation step. In other words, annealing treatment may be added after the termination of the nucleic acid amplification or the nucleic acid amplification may be stopped at the annealing step.

The method for making measurement of a nucleic acid includes the following embodiments.

A. A fluorescence-labeled single-stranded nucleic acid probe is mixed with a sample, and a change in the degree of fluorescence polarization between before and after formation of a double strand is detected thereby to detect the target base sequence present in the nucleic acid of the sample and complementary to the single-stranded nucleic acid probe.

B. A target nucleic acid in a sample and a fluorescence-labeled single-stranded nucleic acid probe having a homologous base sequence to the target nucleic acid are made to compete in hybridizing with a reagent having a nucleic acid containing a base sequence complementary to the target nucleic acid immobilized on a carrier to form a double strand DNA-DNA or DNA-RNA, and a change in the degree of fluorescence polarization between before and after formation of the double strand is measured thereby to detect the base sequence present in the nucleic acid of the sample and complementary to the nucleic acid probe.

C. A target nucleic acid in a sample and a reagent having a nucleic acid whose base sequence is homologous to that of the target nucleic acid immobilized on a carrier are made to compete in hybridizing with a fluorescence-labeled single-stranded nucleic acid probe whose base sequence is complementary to the target nucleic acid to form a double strand DNA-DNA or DNA-RNA, and a change in the degree of fluorescence polarization between before and after formation of the double strand is measured thereby to detect the base sequence present in the nucleic acid of the sample and complementary to the nucleic acid probe.

In carrying out hybridization between the nucleic acid in a sample and a fluorescence-labeled reagent according to the present invention, it is preferred for the system for hybridization to contain 0.01 to 5 mol/l, particularly 0.05 to 3 mol/l, of an organic or inorganic acid salt by adding it before or after mixing of a fluorescence-labeled reagent. If the acid salt concentration is less than 0.01 mol/l, it takes about 30 minutes or longer for reaching saturation of hybridization. It is difficult for many organic or inorganic acid salts to be dissolved in concentrations exceeding 5 mol/l.

Examples of suitable inorganic acid salts include an alkali metal, alkaline earth metal or ammonium salt of hydrochloric acid, carbonic acid or phosphoric acid, such as sodium chloride, potassium chloride, magnesium chloride, zinc chloride, sodium carbonate, calcium carbonate, and sodium phosphate. Examples of suitable organic acid salts include an alkali metal, alkaline earth metal or ammonium salt of acetic acid, citric acid, benzoic acid or phenol.

For the salt be present in the solution in a concentration of 0.01 to 5 mol/l, it may be added previously to either one or both of a reagent and a sample to be assayed, or a reagent or a sample may be diluted with a buffer, etc. containing the salt, or a solution containing the salt may be added to the mixture of a sample and a reagent. In general, salts have a very high constant of dissociation, these salts added to the solution are present in a dissociated state, i.e., as a cation and an anion.

The fluorescence-labeled reagent according to the present invention comprises a substance which specifically binds to the nucleic acid to be detected and a fluorescent label connected to such a substance. Examples of the substance which specifically binds to the nucleic acid to be detected include a nucleic acid having a base sequence complement to the nucleic acid to be detected or other substances (e.g., PNA and nucleic acid-binding protein) which specifically bind to the nucleic acid to be detected.

The fluorescent label which can be used for labeling a reagent include fluorescein, fluorescein isothiocyanate, and tetramethylrhodamine isothiocyanate. These fluorescent substances can be linked to a nucleic acid through, for example, covalent bonding, such as thiocarbamide bonding. For example, a DNA is synthesized by the phosphoramidite method and labeled with a fluorescent label, such as fluorescein.

The base number of the nucleic acid moiety of the fluorescence-labeled reagent and the base number of the nucleic acid to be detected are not particularly limited. Generally, the base number of the fluorescence-labeled reagent enough for detecting a specific gene is from about 20 to about 30 (cf. *Eur. J. Clin. Microbiol. Infect. Dis.*, Vol. 10, pp. 1048–1055 (1991) and Nei, M. and Li, W. H., *Proc. Natl. Acad. Sci. USA*, Vol. 76, pp. 5269–5273 (1979)). The sequence employed for the nucleic acid moiety of the fluorescence-labeled reagent is appropriately selected taking the self-folding of the nucleic acid moiety, complementation with the nucleic acid to be detected, avoidance of binding with the primers, etc. into consideration.

The nucleic acids of a sample which can be detected according to the present invention include those of bacteria and viruses of samples (e.g., serum, urine and various cultures), tissue cells, and free nucleic acids thereof.

Buffers in which hybridization between a nucleic acid of a sample and a fluorescence-labeled reagent is carried out include a Tris buffer, a phosphate buffer, and a citrate buffer. These buffers may contain sodium azide, EDTA, etc. in addition to the above-mentioned organic or inorganic acid salt.

The carrier for immobilization which can be used in the present invention include beads or latex particles of synthetic resins, such as polystyrene and nylon, glass beads, and metal particles, such as Au and Ag. Polymer substances, such as protein, are also useful. The molecular weight of the solid carrier should be selected so that the molecular weight of a complementary nucleic acid may be sufficiently larger than that of the fluorescence-labeled reagent in view of the principle of the fluorescence polarization technique. The molecular weight of the carrier for immobilization is preferably more than 5 times as much as that of the fluorescence-labeled nucleic acid.

A nucleic acid can be bound to the carrier for immobilization by adsorption, covalent bonding, or by utilizing specific affinity between avidin and biotin.

The mechanism of the fluorescence polarization assay will be explained briefly. Wavelengths exciting a fluorescent substance contained in a labeled reagent are isolated from light emitted from a light source by means of a filter and made into linear polarized light through a polarizer. The polarized light is directed to a cell containing a sample to excite a fluorescent substance in the sample. The excited fluorescent substance emits fluorescence having wavelengths inherent to the substance, which fluorescence shows dispersion of the plane of polarization in proportion to the degree of Brownian movement. The fluorescence from the cell passes through a filter transmitting the wavelengths and then a polarizer and converted to electric signals by means of an optical detector. By rotating the polarizer on the fluorescence side, a polarized light component Ia of the fluorescence which has the same direction as the exciting polarized light and a polarized light component Ib which is perpendicular to the component Ia are measured, from which the degree of fluorescence polarization P of the sample to be assayed is calculated according to equation:

$$P = \frac{Ia - Ib}{Ia + Ib}$$

wherein Ia is a polarized light component of the same direction as the exciting polarized light; and Ib is a polarized light component perpendicular to the component Ia.

The more vigorous the Brownian movement of the fluorescent substance or a substance bound to the fluorescent substance, the larger the polarized light component Ib perpendicular to the exciting polarized light and, at the same time, the smaller the polarized light component Ia parallel with the exciting polarized light. As a result, the degree of polarization P decreases.

In carrying out the present invention, a solution containing a fluorescence-labeled complementary nucleic acid is put in a sample cell, and a solution of an assay sample containing a nucleic acid to be assayed is added thereto, and, if desired, a solution containing an immobilized nucleic acid is added. The order of adding these two (or three) solutions is not limited. Before, during or after mixing the assay sample and the fluorescence-labeled reagent, an organic or inorganic acid salt is added. The concentration of the fluorescence-labeled nucleic acid and the immobilized nucleic acid, if used, are selected appropriately according to the desired concentration range of the target nucleic acid.

In the present invention, the fluorescence-labeled complementary nucleic acid is used for specific binding to a target nucleic acid. Therefore, it is possible to substitute the fluorescence-labeled nucleic acid with a fluorescence-labeled substance likewise capable of being specifically bound to the target nucleic acid, for example, peptide nucleic acid (PNA) (see *Perspective Biosystems*, U.S.A.).

A fluorescence polarization technique is sometimes designated a fluorescence depolarization technique, which can be seen as practically the same as the former. In many cases, the degree of fluorescence polarization and the degree of fluorescence depolarization used as the respective measures are also practically the same.

The present invention will now be illustrated in greater detail with reference to Examples, but it should be understood that the present invention is not construed as being limited thereto. In Examples, the present invention was applied to an attempt to rapid detection of VT2-producing *E. coli* O157.

EXAMPLE 1

Nucleic acid in a sample was amplified by the asymmetric PCR method or the conventional PCR method. The amounts of the amplified nucleic acid in samples were respectively subjected to the fluorescence polarization measurements for comparison. As the base sequence of primers, those shown in SEQ ID NO:2: and SEQ ID NO:3: were employed in accordance with Lin Z, et al, *Microbiol Immunol.*, Vol. 37, pp. 543–548 (1993). The length to be amplified is 905 bases.

1) Sample

A sample originated in the beef which had been purchased at Central Wholesale Market in Hiroshima, Japan and from which enterohemorrhagic *E. coli* O157 had been detected was cultured for enrichment in a bouillon medium at 42° C. for about 24 hours and heat treated at 100° C. Whether the sample is O157 positive or negative had been separately confirmed by a conventional culture method.

2) Amplification 2-1) Asymmetric PCR Method

The asymmetric PCR was carried out with equipment available from Perkin Elmer Co., GeneAmp PCR System 9600, MicroAmp Reaction Tube (0.2 ml), by using a reaction solution having the following composition.

| Composition of PCR Solution: | |
|---|---|
| x10 Ex Taq[*1] buffer | 10 μl |
| dNTP mixture (each 2.5 mmol/l) | 8 μl |
| Sample (as amplified) | 1 μl |
| Primer a (10 pmol/μl) | 1 μl |
| Primer b (10 pmol/μl) | 10 μl |
| Takara Ex Taq[*1] (5 units/μl) | 0.5 μl |
| Sterilized distilled water | 69.5 μl |
| Total | 100 μl |

[*1]Taq DNA polymerase available from Takara Co., Ltd., Code No. RROO1A.

The base sequences of the primers a and b are shown in SEQ ID NO:2: and SEQ ID NO:3: in the Sequence Listing.

The DNA to be amplified was denatured at 94° C. for 1 minute into single-stranded DNA, and then the following cycle of operations (i) to (iii) was repeated 40 times, followed by cooling with ice to 4° C.

(i) Thermal denaturation at 94° C. for 30 seconds.
(ii) Annealing of primers a and b to the single-stranded DNA at 45° C. for 30 seconds.
(iii) Extension of DNA with the Taq polymerase at 72° C. for 1 minute.

2-2) Conventional PCR Method (Symmetric PCR Method)

Conventional PCR was carried out under the same conditions as in the asymmetric PCR except that the amounts of primer b and sterilized distilled water in the PCR solution were changed to 1 μl and 78.5 μl, respectively.

3) Preparation of Fluorescence-labeled Reagent

An oligonucleotide comprising 23 bases the sequence of which is shown in SEQ ID NO:1:, which is a part of the gene of Verotoxin (VT2) produced by enterohemorrhagic *E. coli* O157, was synthesized with a DNA synthesizer. The 5'-terminal of the synthetic oligonucleotide was labeled with fluorescein. The resulting fluorescence-labeled oligonucleotide was diluted with a TE buffer (10 mM Tris-HCl (pH 8.0), 1 mM EDTA, and 0.8 M NaCl) to a concentration of 1 nM to prepare a fluorescence-labeled reagent.

4) Measurement of Degree of Fluorescence Polarization

The gene-amplified sample (80 μl) prepared above was mixed with the fluorescence-labeled reagent (400 μl), and 10 minutes later the degree of fluorescence polarization was measured.

As control 1, a solution containing salmon sperm DNA in the same amount as the nucleic acid in the assay sample was subjected to asymmetric PCR amplification in the same manner as in (2-1), and the amount of the amplified nucleic acid was measured in the same manner as described above.

As control 2, the same sample containing the nucleic acid of *E. coli* O157 (after enrichment culture) was assayed in the same manner as described above except that gene amplification was not conducted.

Three tests were made for each sample.

5) Test Results

The graph in FIG. 1 shows plots of the changes in degree of fluorescence polarization P of the sample having been subjected to asymmetric PCR amplification (♦), the sample having been subjected to conventional PCR amplification (■), control 1 (Δ), and control 2 (○) against time. It is seen that the degree of fluorescence polarization of each sample reaches a stationary state in about 10 minutes from the commencement of measurement (the initiation of hybridization of the fluorescence-labeled reagent to the sample nucleic acid), exhibiting clear distinctions among the samples.

Figure 2:
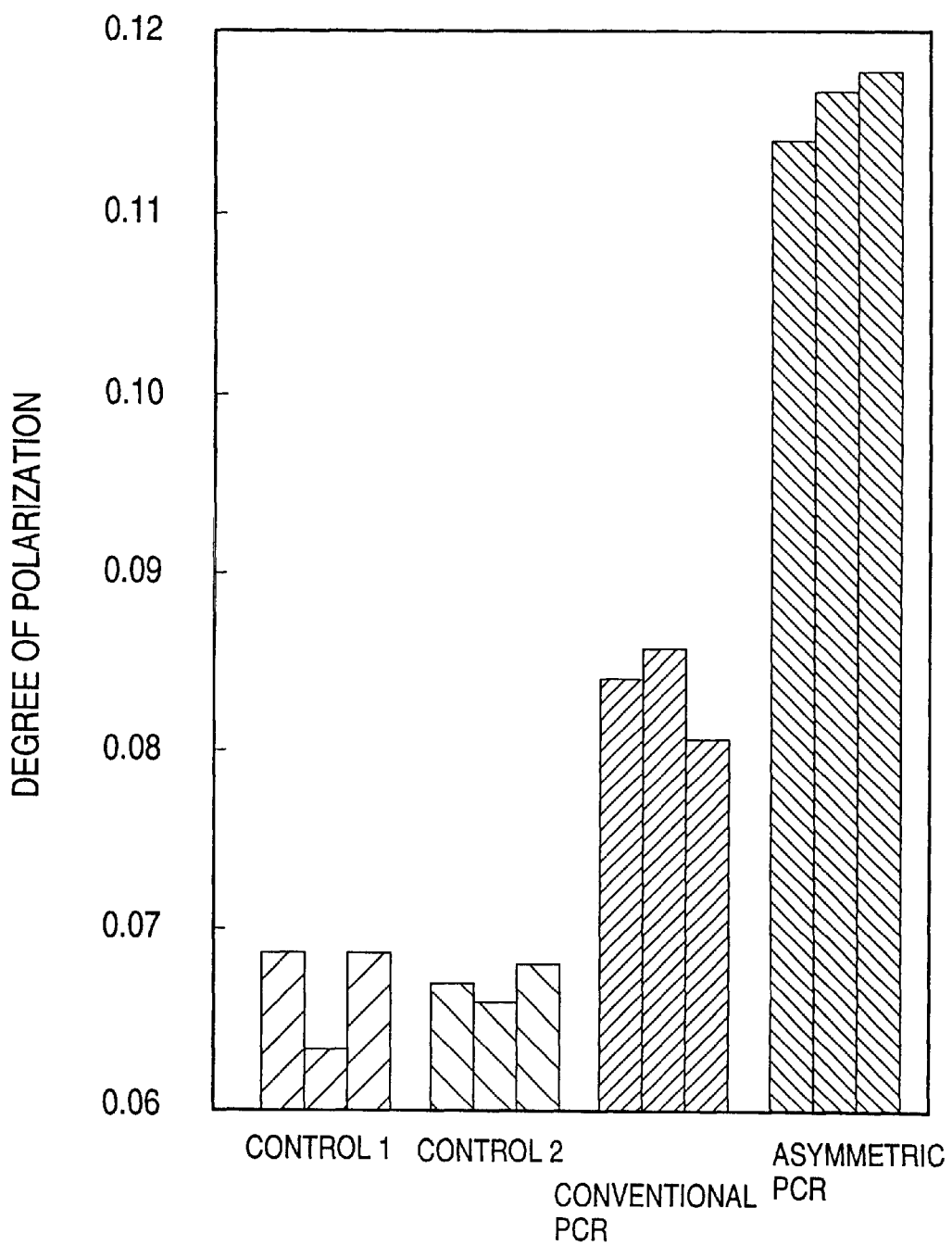
FIG. 2 is a graph showing the degree of fluorescence polarization after 10 minutes from the start of measurement in samples assayed in Example 1.

The degree of fluorescence polarization P of each sample (n=3) after 10 minutes from the start of the measurement is shown in FIG. 2. As can be seen from FIGS. 1 and 2, controls 1 and 2 show no increase in fluorescence polarization degree, and the fluorescence polarization degree of the group of samples having been amplified by conventional PCR was higher than that of control 2 but far lower than that of the group of the samples having been amplified by asymmetric PCR.

It is thus proved that the detection sensitivity of the fluorescence polarization technique can be greatly improved by amplifying the nucleic acid in a sample by asymmetric PCR.

Figure 3:
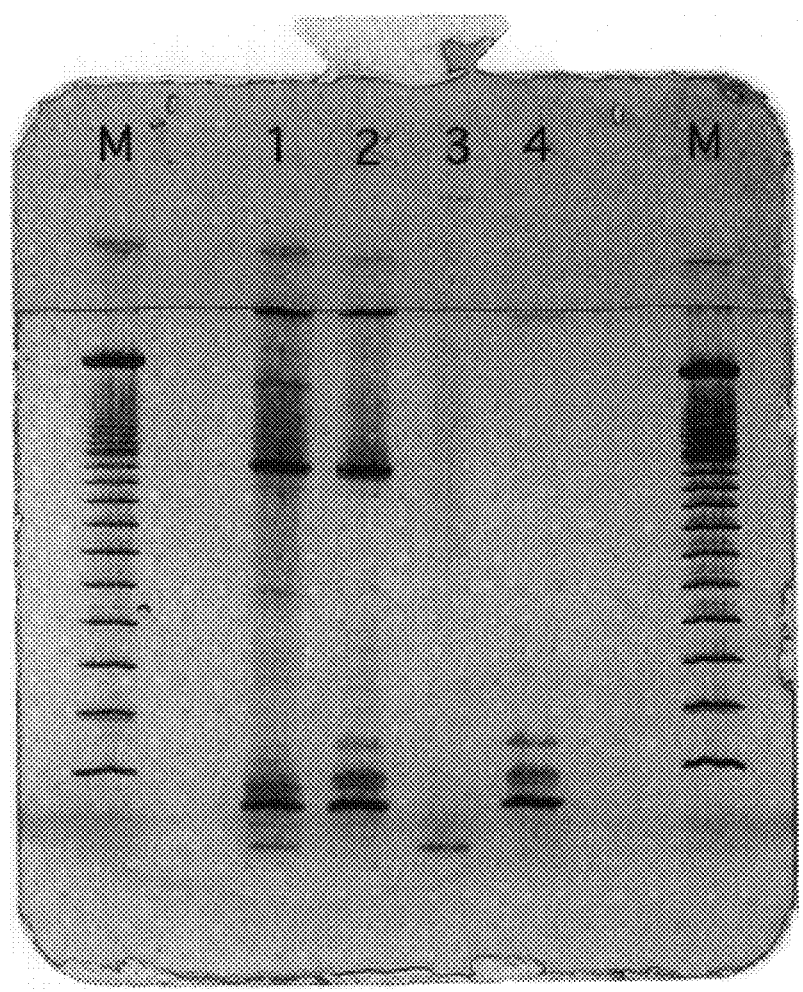
FIG. 3 is the electrophoresis pattern of samples after gene amplification.

FIG. 3 shows the pattern of polyacrylamide gel electrophoresis analysis (detection: silver staining), from which the results of gene amplification can be confirmed. Lane 1 is an O157 positive sample amplified by symmetric PCR; lane 2 is an O157 positive sample amplified by asymmetric PCR; lane 3 is an O157 negative sample amplified by symmetric PCR; and lane 4 is an O157 negative sample amplified by asymmetric PCR. All the samples had been enrichment cultured for about 24 hours and heat treated prior to gene amplification.

The length subject to gene amplification by PCR is over 900 bases. The samples of lanes 1 and 2 show a band at this position, indicating amplification of the target DNA. The lane on both sides is a ladder marker for every 100 bases.

EXAMPLE 2

The nucleic acid in the same sample as used in Example 1 was amplified by symmetric PCR and denatured into a single-stranded nucleic acid, and then the primers used in the amplification were subjected to annealing. The amplified nucleic acid was measured by the fluorescence polarization technique, and the results were compared with those obtained from the sample in which the primers were not subjected to annealing. The symmetric PCR and the detection by fluorescence polarization were carried out under the same conditions as in Example 1. The annealing of the primers used for amplification was conducted under the same annealing conditions as employed in the repetition of PCR replication.

As control 3, the same procedure was repeated on a sample solution containing salmon sperm DNA in the same amount as the nucleic acid in the assay sample.

As control 4, nucleic acid assay was made in the same manner except that the nucleic acid of the assay sample was not amplified.

Figure 4:
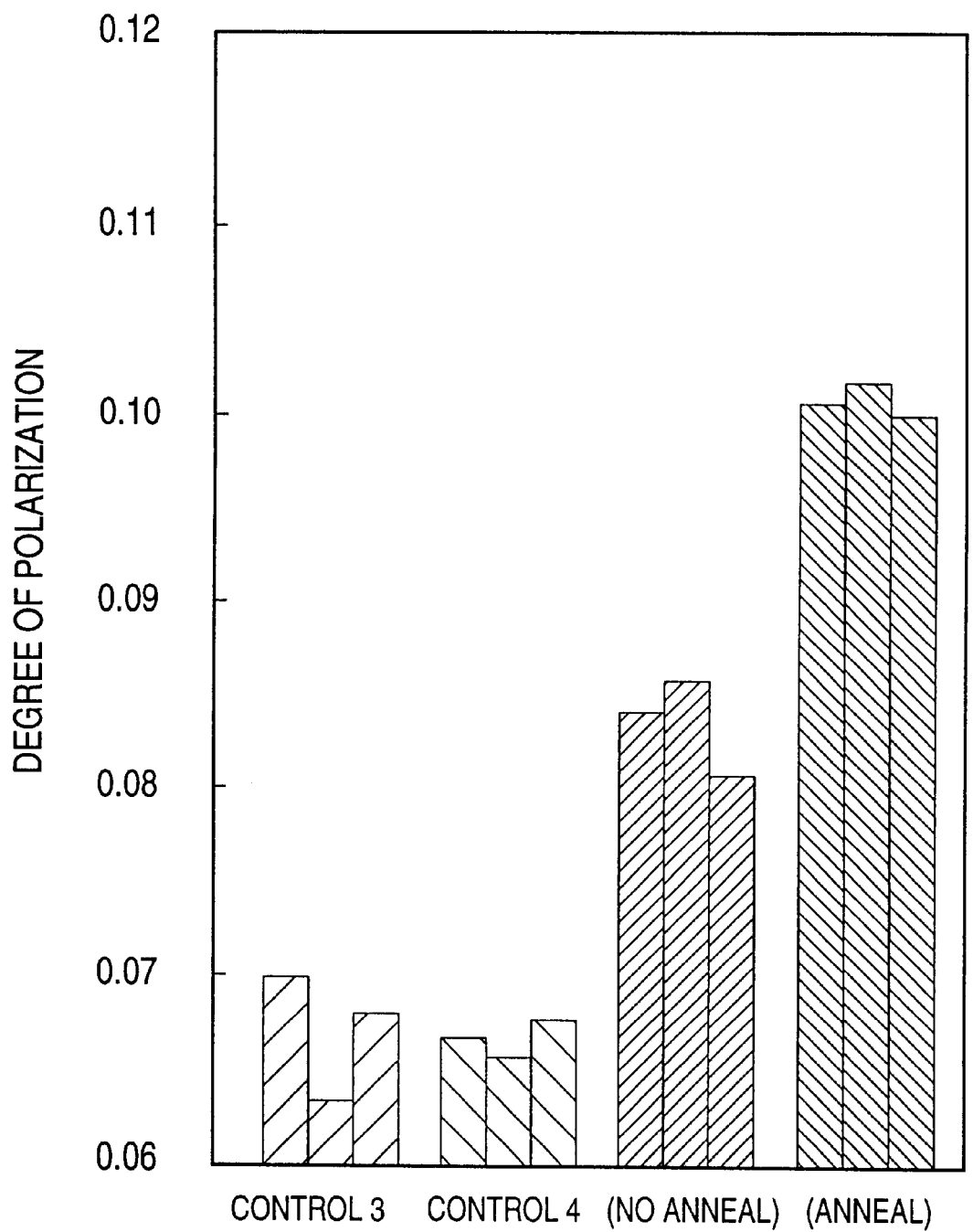
FIG. 4 is a graph showing the degree of fluorescence polarization after 10 minutes from the start of measurement in samples assayed in Example 2.

FIG. 4 shows the degree of fluorescence polarization P after 10 minutes from the start of measurement, of the samples having been subjected to the primer annealing, the samples not having been subjected to the primer annealing, control 3, and control 4. No increase in fluorescence polarization degree was observed with control 3 or 4. The fluorescence polarization degrees of the samples not having been subjected to the primer annealing, while higher than those of controls 3 and 4, were far lower than those of the samples having been subjected to the primer annealing.

The reproducibility of measurement having been increasing in the laboratory, the inventors have succeeded in assaying by the fluorescence polarization technique in 10 minutes on samples having been enrichment cultured for about 1 day and subjected to gene amplification for about 2 hours.

As described above, the DNA assay making use of fluorescence polarization has a great possibility as a rapid and simple method of assay.

While the invention has been described in detail and with reference to specific examples thereof, it will be apparent to one skilled in the art that various changes and modifications can be made therein without departing from the spirit and scope thereof.

This application is based on Japanese patent application Hei-9-219744, filed on Aug. 1, 1997, incorporated herein by reference.

What is claimed is:

1. A method for assaying for the presence of a target double-stranded nucleic acid in a sample which comprises:
   (A) amplifying a target double-stranded nucleic acid in a sample by asymmetric amplification, wherein said asymmetric amplification is carried out by PCR using a first primer which is used to produce a single-stranded nucleic acid having a nucleotide sequence which is complementary to a fluorescence-labelled probe, and a second primer, and wherein said first primer is used in an amount two to ten times that of said second primer,
   (B) annealing a fluorescence-labelled probe to the resulting amplified nucleic acid of step (A) in a reaction solution containing 0.01 to 5 mol/l of an organic or inorganic acid salt, wherein said fluorescence-labelled probe is complementary to said amplified nucleic acid, and
   (C) detecting annealing of said probe by fluorescence polarization so as to detect the presence of said target double-stranded nucleic acid.

2. A method for detecting a Verotoxin-producing microorganism in a sample, which comprises detecting a nucleic acid which is specific to a Verotoxin-producing microorganisms by the method according to claim 1.

3. A method for detecting a Vertoxin-producing microorganism in a sample according to claim 2, wherein the fluorescence-labeled probe consists of a DNA molecule represented by the nucleotide sequence AGTATCGGG-GAGAGGATGGTGTC (SEQ ID NO: 1).

4. The method of claim 1, wherein said reaction solution of step (B) contains 0.05 to 3 mol/l of an organic or inorganic acid salt.

5. The method of claim 1, wherein said organic or inorganic acid salt is an inorganic acid salt.

6. The method of claim 1, wherein said inorganic acid salt is selected from the group consisting of sodium chloride, potassium chloride, and a mixture thereof.

* * * * *

SEQUENCE LISTING

<160> NUMBER OF SEQ ID NOS: 3

<210> SEQ ID NO 1
<211> LENGTH: 23
<212> TYPE: DNA
<213> ORGANISM: synthetic construct

<400> SEQUENCE: 1
agtatcgggg agaggatggt gtc                                        23

<210> SEQ ID NO 2
<211> LENGTH: 20
<212> TYPE: DNA
<213> ORGANISM: synthetic construct

<400> SEQUENCE: 2
gaacgaaata atttatatgt                                            20

<210> SEQ ID NO 3
<211> LENGTH: 18
<212> TYPE: DNA
<213> ORGANISM: synthetic construct

<400> SEQUENCE: 3
tttgattgtt acagtcat                                              18